United States Patent [19]

Donehoo et al.

[11] Patent Number: 5,660,184
[45] Date of Patent: Aug. 26, 1997

[54] PACEMAKER PULSE DETECTION AND ARTIFACT REJECTION

[75] Inventors: Robert F. Donehoo, Lutz; David W. Browne, Tampa, both of Fla.

[73] Assignee: Johnson & Johnson Medical, Inc., New Brunswick, N.J.

[21] Appl. No.: 440,903

[22] Filed: May 15, 1995

[51] Int. Cl.$^6$ ................................................. A61B 5/024
[52] U.S. Cl. ................................................. 128/696
[58] Field of Search ................. 364/413.06; 607/27; 128/696, 697, 701, 704, 708, 901

[56] References Cited

U.S. PATENT DOCUMENTS

| | | | |
|---|---|---|---|
| 4,934,376 | 6/1990 | Armington | 128/697 |
| 5,012,814 | 5/1991 | Mills et al. | 128/697 |
| 5,033,473 | 7/1991 | Wang et al. | 128/696 |

*Primary Examiner*—William E. Kamm
*Assistant Examiner*—George R. Evanisko
*Attorney, Agent, or Firm*—Woodcock Washburn Kurtz Mackiewicz & Norris LLP

[57] ABSTRACT

A method and apparatus for detecting a pacemaker pulse in an electrocardiogram signal (ECG signal) from characteristic artifacts introduced into said ECG signal by the filtering process to allow identification and removal of the pacemaker pulse from the ECG signal. Upon detection of the pacemaker event, the amplitude threshold used in the detection of the QRS complex is raised to a higher level following the pacemaker pulse so that the characteristic artifacts do not exceed the threshold. The amplitude threshold is decayed to the normal QRS threshold level over a time interval determined in accordance with the characteristics of the filter which introduced the artifacts so that the artifacts will remain below the amplitude threshold. This technique is desired since prior art techniques requiring removal of the pacemaker pulse and any artifacts associated with the pacemaker pulse before QRS complex detection also remove any QRS complexes occurring in the blanking window. By using a variable threshold, the amplitude of the QRS complex will exceed the threshold while the artifacts caused by the pacemaker pulse will remain below the threshold so that no blanking is necessary.

8 Claims, 5 Drawing Sheets

PACEMAKER PULSE DETECTION AND ARTIFACT REJECTION

FIELD OF THE INVENTION

This invention relates to a method and apparatus for detecting pacemaker pulses in electrocardiogram signals and for eliminating from electrocardiogram signals artifacts introduced by such pacemaker pulses, and, more particularly, to a technique for detecting pacemaker pulses from characteristic artifacts introduced by filtering of the pacemaker pulses and for providing an adjustable threshold which prevents false detection of QRS complexes in the electro-cardiogram signal because of the pacemaker pulses and their artifacts.

BACKGROUND OF THE INVENTION

Electrocardiographs (ECGs) with pacemaker detection capability are known in the art. Since the pacemaker pulse is generally a high frequency, large amplitude pulse, conventional ECGs with pacemaker detection capability typically detect the pacemaker pulse using hardware which compares the electrocardiogram signal to an amplitude threshold. Then, once the pacemaker pulse is detected, the portion of the electrocardiogram signal containing the pacemaker pulse and any artifacts such as overshoot and ringing associated with filtering of the pacemaker pulse are blanked (removed) from the electrocardiogram signal using gates and the like before the electrocardiogram signal is processed. The QRS detection portion of the ECG monitor is then notified that there was a pacemaker event at the blanked portion of the waveform. Unfortunately, removal of the pacemaker pulse and its artifacts often has the unintended result of removing any QRS complexes which occur during the same time window.

On the other hand, prior art ECG monitors which detect pacemaker pulses but do not blank (remove) the artifacts associated with each pacemaker pulse before it enters any filtering process may cause QRS complexes to be falsely detected if the patient's heart does not respond to the pacemaker. Also, since QRS detectors are allowed by regulatory standards to detect signals as small as 0.15 mV, the artifacts following a pacemaker pulse can be large enough to be counted as a heart beat under some circumstances. This result is obviously undesirable.

Many prior art ECG monitors accomplish these pacemaker detection and rejection tasks using specially designed circuitry. Unfortunately, such systems are typically quite costly and relatively inflexible. Other ECG monitors typically determine the extent of the pacemaker artifact using a hardware detection circuit and then blank out a region following the pacemaker pulses using a software routine so that the artifacts following the pacemaker pulses do not falsely trigger the QRS detection portion of the ECG monitor. The period of time that must be blanked is determined by the hardware filter characteristics and can be quite long, for example, 45 ms. As in the prior art hardware embodiments, in addition to removing the artifact from the signal going to the QRS detector, the users are deprived of any information in the electrocardiogram signal (such as QRS complexes) which occur during the blanked interval.

Accordingly, it is desired to overcome these problems in the prior art by blanking only the pacemaker pulse and by adjusting the QRS detection operation so that pacemaker artifacts in a time window following detected pacemaker pulses do not cause false QRS complex detections. The present invention has been designed to meet these needs in the art.

SUMMARY OF THE INVENTION

A device and a method are described which meet the above-mentioned needs in the art by providing an electrocardiograph (ECG) monitor which detects a pacemaker pulse in a digitized and filtered electrocardiogram signal based on the characteristic artifacts introduced into the electrocardiogram signal by the filtering process. QRS complexes in the electro-cardiogram signal are then detected by comparing the filtered, digitized electrocardiogram signal to a variable amplitude threshold. In accordance with the invention, the amplitude threshold has a first level related to the amplitude of the patient's QRS complexes and a second level, greater than the first level, which is used for a time interval immediately after detection of a pacemaker pulse. Preferably, the amplitude threshold decays from the second level to the first level over a predetermined amount of time after the pacemaker event so as to substantially prevent characteristic "ringing" artifacts caused by filtering of the pacemaker event from being detected as a QRS complex. Generally, the second level and the predetermined amount of time are set in accordance with known artifact producing characteristics of the filter which created the artifacts. The pacemaker event and the characteristic artifacts may then be ignored without missing any QRS complexes which occur in the same time window.

BRIEF DESCRIPTION OF THE DRAWINGS

The present invention will be better understood after reading the following detailed description of the presently preferred embodiments thereof with reference to the appended drawings, of which.

DETAILED DESCRIPTION OF THE PRESENTLY PREFERRED EMBODIMENT

A system and method which meets the above-mentioned objects and provides other beneficial features in accordance with the presently preferred exemplary embodiment of the invention will be described below with reference to FIGS. 1–7. Those skilled in the art will readily appreciate that the description given herein with respect to those figures is for explanatory purposes only and is not intended in any way to limit the scope of the invention. All questions regarding the scope of the invention should be resolved by referring to the appended claims.

Figure 1:
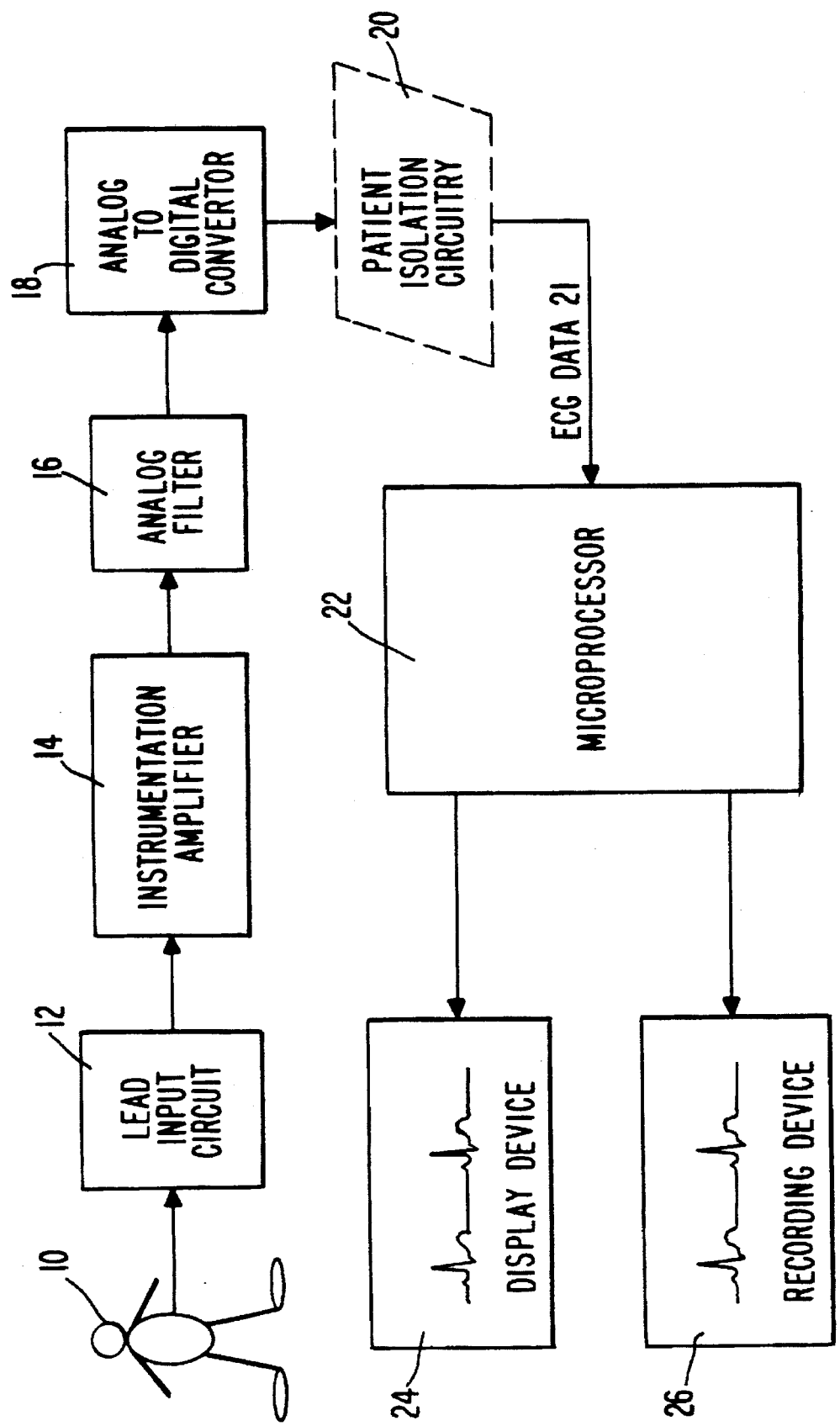
FIG. 1 illustrates an electrocardiograph (ECG) monitor modified to include the pacemaker pulse detection and artifact rejection techniques of the invention.

FIG. 1 illustrates an electrocardiograph (ECG) monitor modified to include the pacemaker pulse detection and artifact rejection techniques of the invention. As illustrated, a patient 10 is connected in a conventional manner to QRS leads from a lead input circuit 12 for detection of the electrocardiogram signal of the patient. The resulting electrocardiogram signal is amplified by instrumentation amplifier 14 and filtered by analog filter 16 to remove noise components before being converted into a digital signal by A/D converter 18. Of course, the electrocardiogram signal can be converted to digital form before being filtered by a digital filter. The resulting digital ECG signal 21 passes through patient isolation circuitry 20 of the type known in the art before being processed by software of microprocessor 22 to calculate heart rate and the like. The processed digital electrocardiogram signal is then displayed on display device 24 and is optionally recorded by recording device 26.

Figure 2:
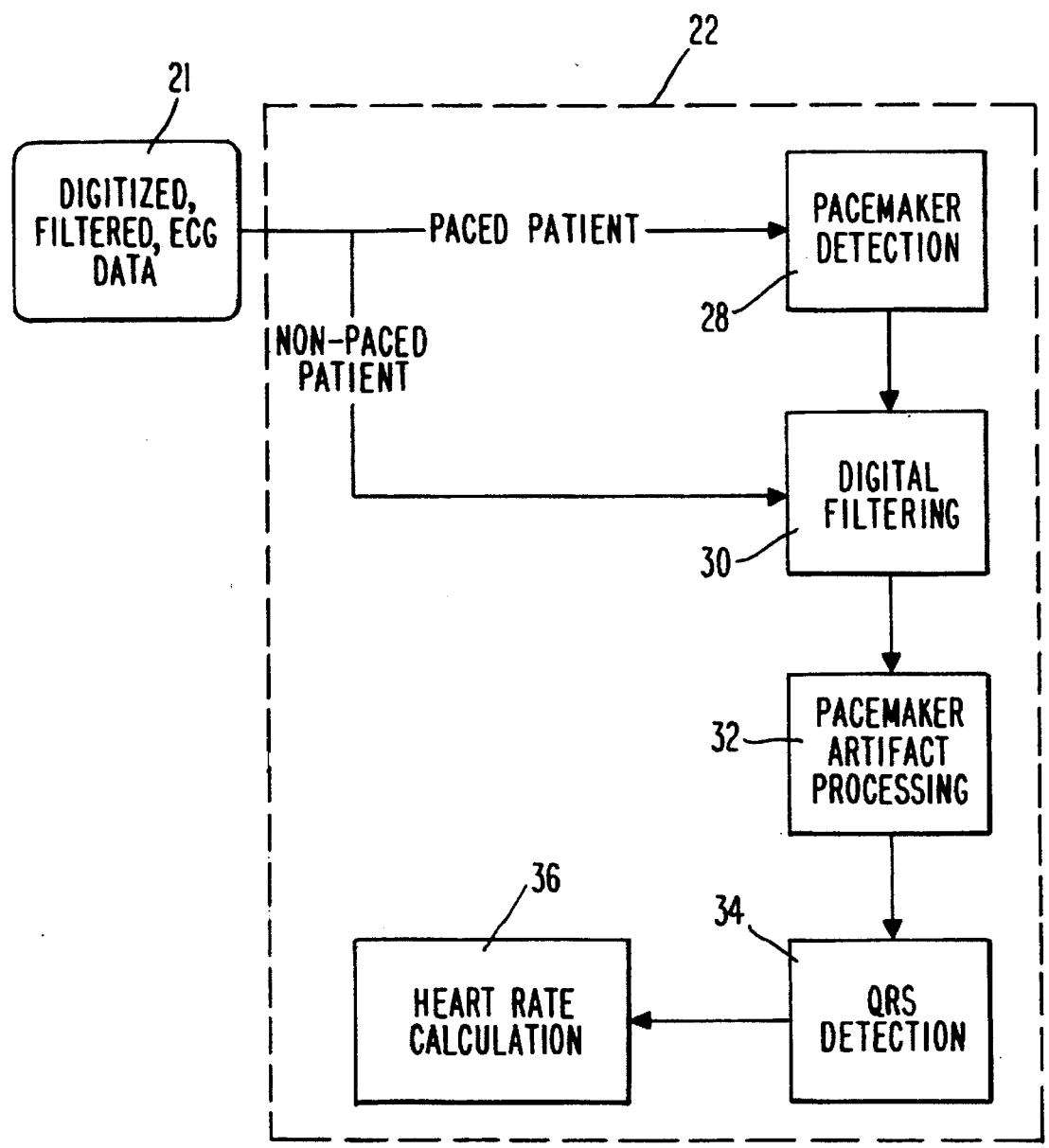
FIG. 2 illustrates a flow chart of the processing performed by microprocessor 22 of the ECG monitor of FIG. 1.

Generally, microprocessor 22 processes ECG signal 21 to detect and remove pacemaker pulses, to eliminate artifacts caused by filtering of the pacemaker pulses, and to calculate the patient's heart rate from the resulting data. FIG. 2 illustrates a flow chart of the processing performed by microprocessor 22. As shown, the ECG signal 21 is processed by pacemaker detection software 28 to detect whether a pacemaker event is present in the ECG signal 21. As indicated, use of pacemaker detection software 28 may be optional, depending upon whether use of a pacemaker by the patient is known. If it is known that the patient does not use a pacemaker, the ECG signal 21 may be applied directly to digital filtering software 30. Otherwise, the ECG signal 21 is processed by pacemaker detection software 28 to detect a pacemaker pulse. Although the pacemaker pulse may be detected using known hardware and software detection techniques of the type mentioned above, it is preferred that the pacemaker pulse be detected by searching for the characteristic overshoot and other filter artifacts introduced into the ECG signal 21 by analog filter 16. This may be done, for example, by comparing the input ECG signal 21 to a template for the analog filter 16. Such an approach is contrary to conventional techniques since the conventional wisdom is that the artifacts should be removed—not used to detect a pacemaker event.

The ECG signal 21 is next filtered by digital filter 30 to remove the high frequency pacemaker pulse. However, as will be explained below, in accordance with the invention, the pacemaker artifacts are not removed by digital filter 30. Instead, the artifacts are allowed to remain so that coincident QRS complexes are not also filtered out.

Next, the ECG signal 21 is processed by pacemaker artifact processing software 32 to remove the artifacts and by QRS detection routine 34 to detect QRS complexes. Such techniques will be described in more detail below with respect to FIGS. 3-7. Finally, the heart rate is calculated from the QRS complexes by heart rate calculation software 36 using conventional techniques.

Figure 3:
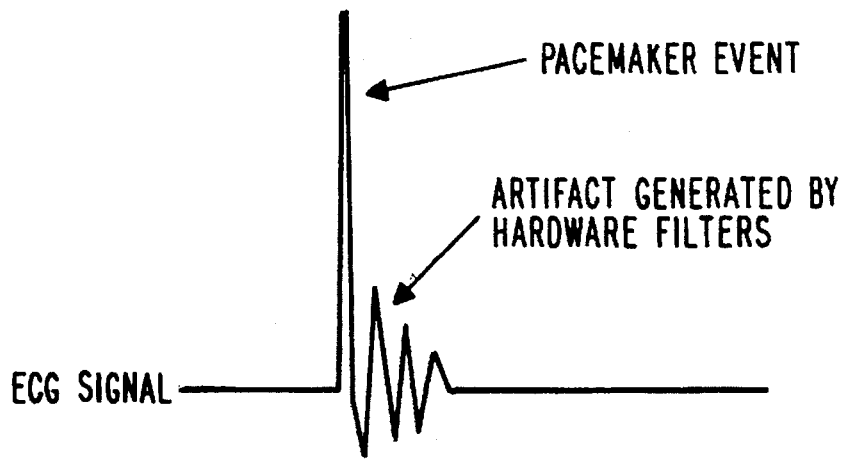
FIG. 3 illustrates a pacemaker pulse and its associated artifacts generated by filters in the ECG monitor.

FIG. 3 illustrates a pacemaker pulse and its associated artifacts generated by filters in the ECG monitor. As noted above, the filters, such as analog filter 16 of the ECG monitor of FIG. 1, introduce characteristic overshoot and ringing artifacts into the ECG signal 21 because of the filtering of the high frequency, large amplitude pacemaker pulse. As noted above, in accordance with the invention, these characteristic artifacts for the particular filter are used to determine that a pacemaker pulse is indeed present in the input ECG signal 21.

Figure 4:
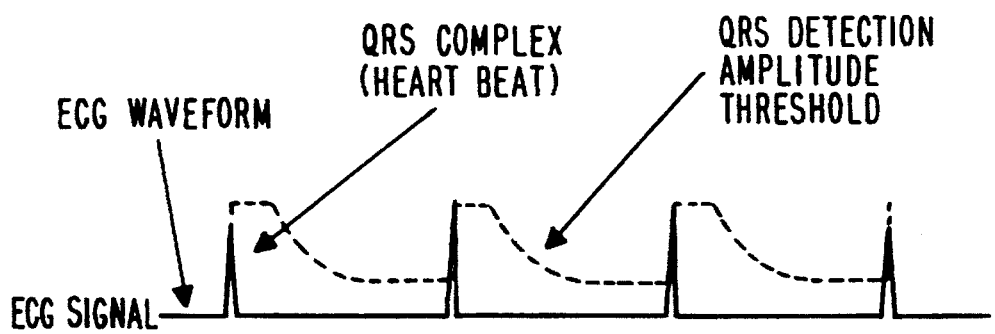
FIG. 4 illustrates an electrocardiogram waveform and a variable threshold used to detect a QRS complex.
Figure 5:
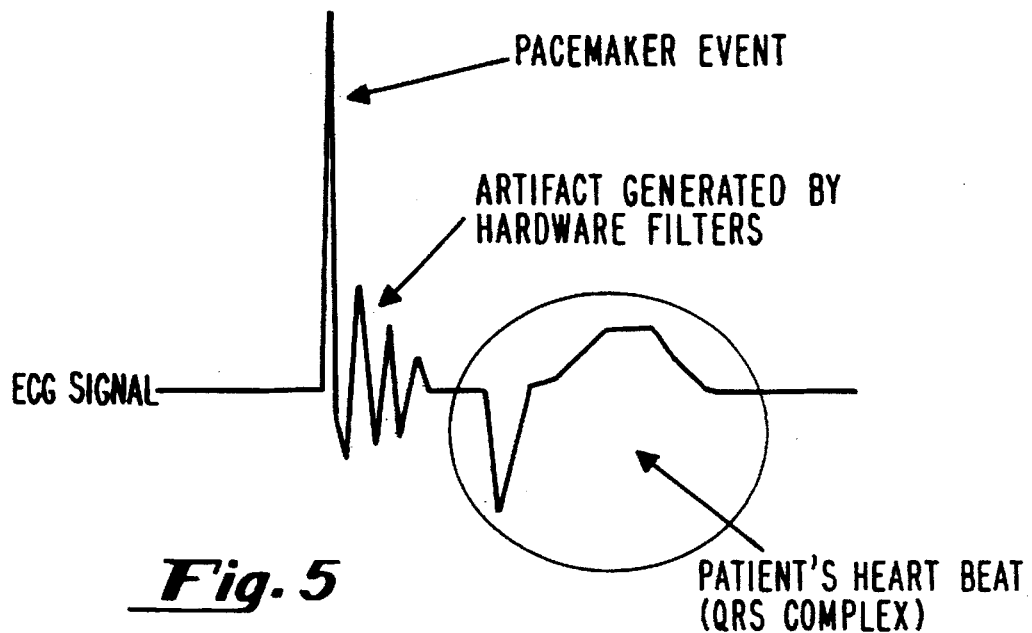
FIG. 5 illustrates an electrocardiogram waveform having a pacemaker pulse and artifacts large enough to be counted as a heart beat under certain circumstances.

QRS detectors in ECG monitors often use amplitude as a basis for detection of heart beats. As shown in FIG. 4, in accordance with the invention, an amplitude threshold is determined from the patient's own QRS complexes as a fraction of the amplitude of the QRS complexes and is decayed over time to allow new QRS complexes to be detected. The resulting amplitude threshold is the dotted line illustrated in FIG. 4. Unfortunately, since QRS detectors are allowed by regulatory standards to detect signals as small as 0.15 mV, artifacts following a pacemaker pulse can be large enough to be counted as a heart beat against such an amplitude threshold under certain circumstances. For example, as illustrated in FIG. 5, the amplitude of the artifacts following the pacemaker pulse may well exceed the amplitude of the QRS complex. Because of this, further modification of the threshold measurement technique is needed to account for the pacemaker artifacts.

Figure 6:
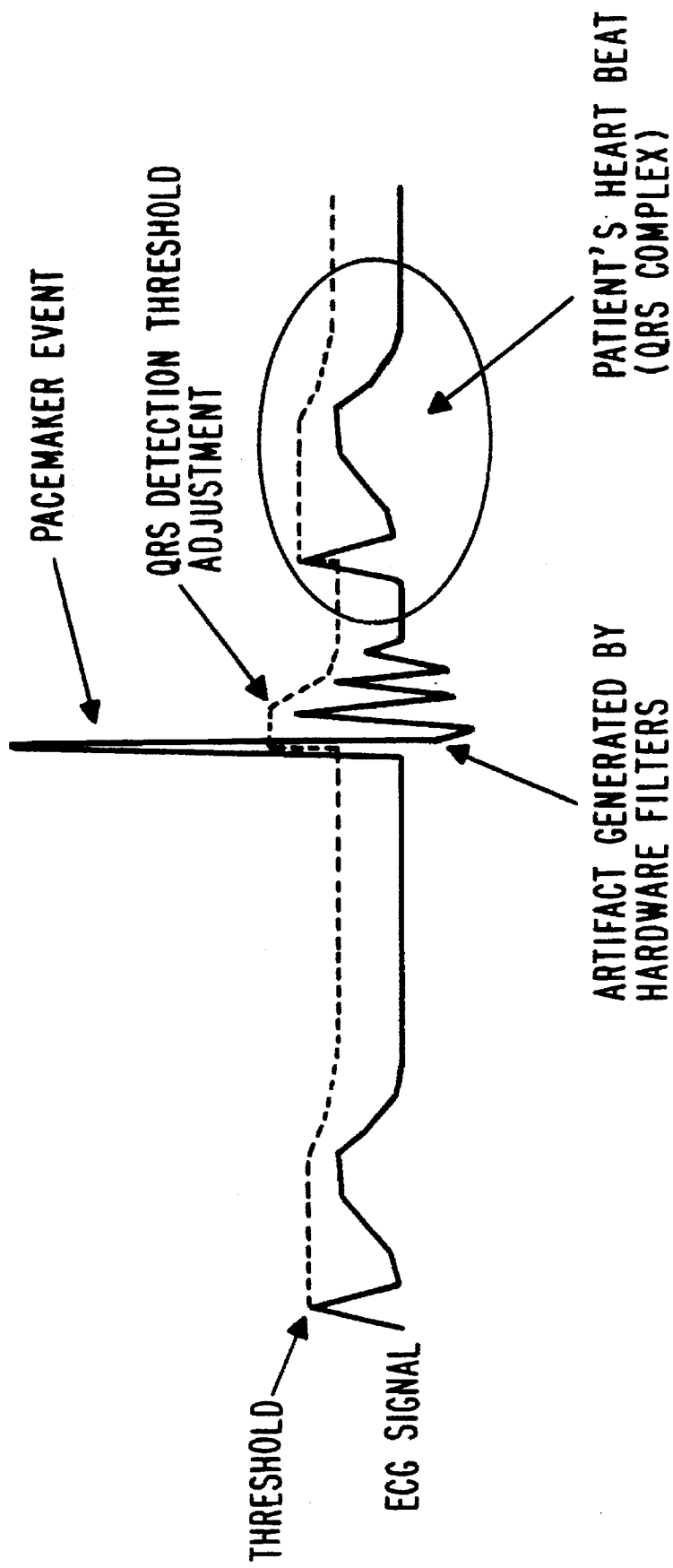
FIG. 6 illustrates an electrocardiogram waveform having a pacemaker pulse and artifacts compared to an amplitude threshold modified in accordance with the invention so that the artifacts are not counted as a heart beat.

FIG. 6 illustrates an electrocardiogram waveform having a pacemaker pulse and artifacts which is compared to an amplitude threshold modified in accordance with the invention so that the artifacts are not counted as a heart beat. As noted above, by characterizing the filters of the ECG monitor, the extent of the artifact following a pacemaker pulse can be determined. Once this information is known, the QRS complex detection amplitude thresholds can be modified following detection of a pacemaker pulse by pacemaker detection software 28 so that the artifacts following a pacemaker pulse are not counted as a heart beat. As shown in FIG. 6, this is accomplished by moving the QRS detection threshold to a level just above the known artifact amplitude characteristic immediately after the known pacemaker pulse and then lowering the QRS detection threshold in such a manner that it stays just above the artifact amplitude characteristic. Over a predetermined amount of time, the QRS detection threshold after a pacemaker pulse is decayed back to the normal level for QRS complex detection. Of course, the amount of time for the decay is dependent on the known artifact amplitude characteristics for the particular filter 16 used by the ECG monitor.

Figure 7:
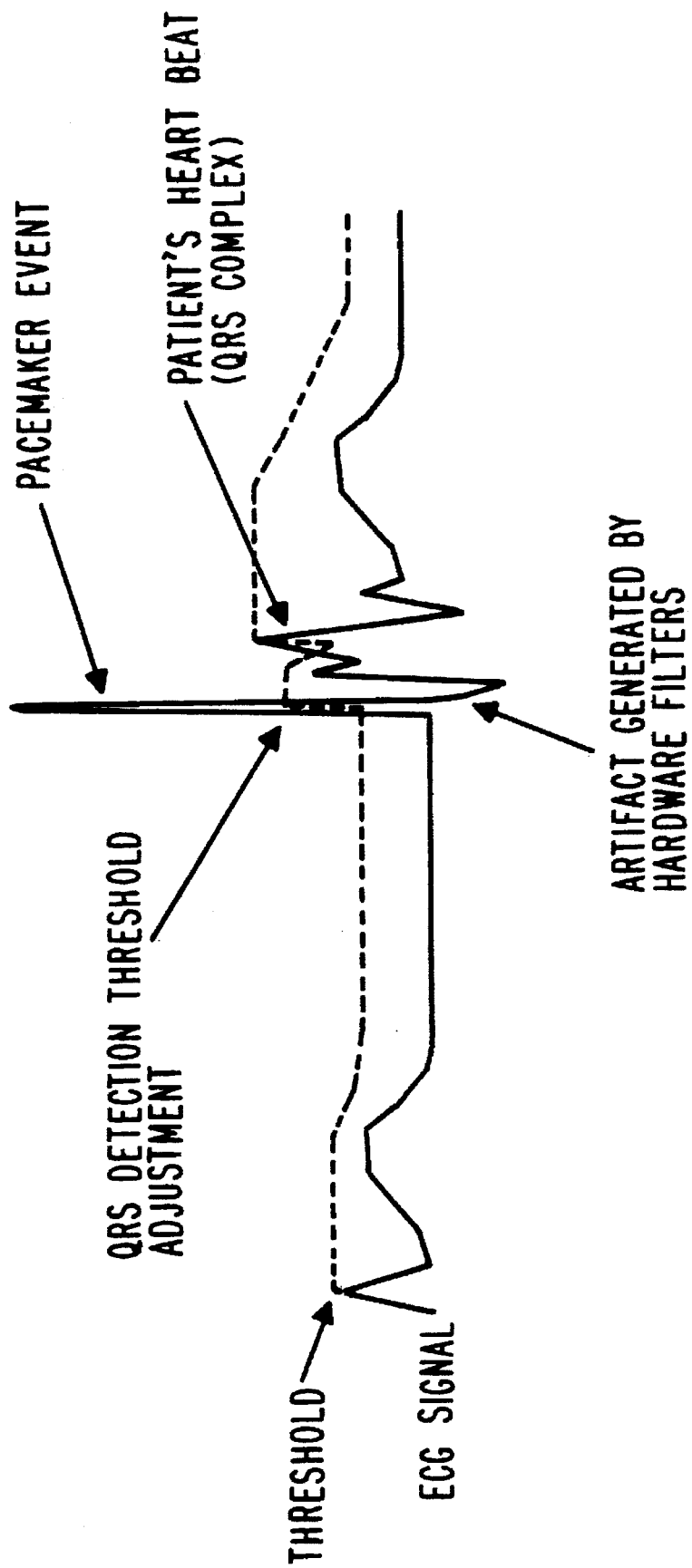
FIG. 7 illustrates an electrocardiogram waveform having a pacemaker pulse and artifacts occurring simultaneously with a QRS complex but an amplitude threshold modified in accordance with the invention to permit detection of the QRS complex despite the artifacts.

Of course, a QRS complex may occur simultaneously with a pacemaker pulse and its artifacts. As noted above, it is important that the QRS complex not be overlooked during the removal of the pacemaker pulse and its artifacts. FIG. 7 illustrates such an electrocardiogram waveform in which the pacemaker pulse and artifacts occur simultaneously with the QRS complex. As shown, since the amplitude threshold after a known pacemaker pulse is modified in accordance with the invention to a level just above the known artifacts, the fact that the artifacts and QRS complex amplitudes will add together to exceed the modified QRS detection threshold will permit detection of the QRS complex despite the artifacts. As in the conventional case (without a pacemaker pulse) illustrated in FIG. 4, the QRS detection threshold would then decay in the normal manner after detection of a QRS complex.

Those skilled in the art will appreciate that the technique of the invention makes it possible to detect a pacemaker pulse in a straightforward way despite any noise in the ECG signal and makes it possible through intelligent control of the QRS amplitude detection thresholds to detect QRS complexes despite the presence of substantial artifacts introduced by filtering of the pacemaker pulse signal. The technique of the invention works for both hardware and software filtering techniques since in each case the artifact characteristics of the filters provide a fingerprint which may be readily used by those skilled in the art to provide a template for matching to similar characteristics in received ECG signals.

Those skilled in the art will also appreciate that the foregoing has set forth the presently preferred embodiment of the invention but that numerous alternative embodiments are possible without departing from the novel teachings and advantages of the invention. Accordingly, all such modification are intended to be included within the scope of the appended claims.

We claim:

1. An electrocardiograph (ECG) monitor which monitors patient's electrocardiogram and detects pacemaker events in said electrocardiogram, said ECG monitor comprising:

means for detecting an electrocardiogram signal of the patient, including any pacemaker events in said electrocardiogram signal;

a filter which filters said electrocardiogram signal and introduces characteristic noise artifacts into said electrocardiogram signal upon filtering of a pacemaker event; and processing means for setting an amplitude threshold, for detecting said pacemaker event in said filtered electrocardiogram signal, and for detecting a QRS complex in said filtered electrocardiogram signal by comparing said filtered electrocardiogram signal to said amplitude threshold, said amplitude threshold having a first level which is a fraction of an amplitude of said patient's QRS complexes and a second level, greater than said first level, immediately after a detected pacemaker event, said amplitude threshold decaying from said second level to said first level over a predetermined amount of time after said detected pacemaker event so as to substantially prevent a false detection of said characteristic noise artifacts as a QRS complex.

2. An ECG monitor as in claim 1, wherein said second level and said predetermined amount of time are set by said processing means in accordance with known noise artifact producing characteristics of said filter.

3. An electrocardiograph (ECG) monitor which monitors a patient's electrocardiogram and detects pacemaker events in said electrocardiogram, said ECG monitor comprising:

means for detecting an electrocardiogram signal of the patient, including any pacemaker events in said electrocardiogram signal;

a filter which filters said electrocardiogram signal and introduces characteristic noise artifacts into said electrocardiogram signal upon filtering of a pacemaker event; and processing means for detecting said pacemaker event in said filtered electrocardiogram signal from the presence of said characteristic noise artifacts introduced into said electrocardiogram signal by said filter.

4. An ECG monitor as in claim 3, wherein said processing means includes means for removing said pacemaker event and said characteristic noise artifacts from said filtered electrocardiogram signal.

5. A method of detecting a QRS complex in an electrocardiogram signal of a patient, comprising the steps of:

detecting said electrocardiogram signal of the patient, including any pacemaker events in said electrocardiogram signal;

filtering said electrocardiogram signal with a filter which introduces characteristic noise artifacts into said electrocardiogram signal upon filtering of a pacemaker event;

detecting said pacemaker event in said filtered electrocardiogram signal;

setting an amplitude threshold, said amplitude threshold having a first level which is a fraction of an amplitude of said patient's QRS complexes and a second level, greater than said first level, immediately after said detected pacemaker event, said amplitude threshold decaying from said second level to said first level over a predetermined amount of time after said detected pacemaker event;

comparing said filtered electrocardiogram signal to said amplitude threshold; and determining that a QRS complex is present when said filtered electrocardiogram signal exceeds said amplitude threshold signal artifacts caused by said pacemaker event as a QRS complex.

6. A method as in claim 5, wherein said step of setting said amplitude threshold includes the step of setting said second level and said predetermined amount of time in accordance with known noise artifact producing characteristics of said filter.

7. A method of detecting a pacemaker event in an electrocardiogram signal of a patient, comprising the steps of:

detecting said electrocardiogram signal of the patient, including any pacemaker events in said electrocardiogram signal;

filtering said electrocardiogram signal with filter which introduces characteristic noise artifacts into said electrocardiogram signal upon filtering of a pacemaker event; and detecting the presence of said characteristic noise artifacts in said filtered electrocardiogram signal as indicative of the occurrence of said pacemaker event immediately prior to said characteristic noise artifacts.

8. A method as in claim 7, comprising the further step of removing said pacemaker event and said characteristic noise artifacts from said filtered electrocardiogram signal.

\* \* \* \* \*